US007897112B2

(12) United States Patent
Mayer (10) Patent No.: US 7,897,112 B2
(45) Date of Patent: Mar. 1, 2011

(54) MULTI-CHAMBER CHEMICAL DELIVERY CONTAINER

(75) Inventor: John J. Mayer, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 739 days.

(21) Appl. No.: 11/767,708

(22) Filed: Jun. 25, 2007

(65) Prior Publication Data

US 2008/0317640 A1    Dec. 25, 2008

(51) Int. Cl.
*B01L 3/00* (2006.01)
(52) U.S. Cl. ............... 422/101; 422/102; 604/6.15; 604/410
(58) Field of Classification Search .............. None
See application file for complete search history.

(56) References Cited

U.S. PATENT DOCUMENTS

| 2,006,085 A | 6/1935 | Lehmkuhl ............... 422/275 |
|---|---|---|
| 4,941,519 A | 7/1990 | Sestak et al. ............ 141/22 |
| 5,209,909 A | 5/1993 | Siegel et al. ............ 422/292 |
| 5,595,711 A | 1/1997 | Wilson et al. ........... 422/119 |
| 5,662,866 A | 9/1997 | Siegel et al. ............ 422/29 |
| 5,759,501 A | 6/1998 | Livingston et al. ....... 422/275 |
| 5,858,305 A | 1/1999 | Malchesky ............. 422/28 |
| 5,863,499 A | 1/1999 | Kralovic .............. 422/332 |
| 5,932,171 A | 8/1999 | Malchesky ............. 422/29 |
| 5,997,814 A | 12/1999 | Minerovic et al. ........ 422/29 |
| 6,158,580 A | 12/2000 | Davis ................ 206/204 |
| 6,325,968 B1 | 12/2001 | Fricker et al. ........... 422/28 |
| 6,482,358 B1 | 11/2002 | Kelsch et al. ........... 422/28 |
| 6,749,807 B1 | 6/2004 | Schindly et al. ......... 422/28 |
| 7,229,599 B2 | 6/2007 | Horacek et al. ......... 422/275 |
| 2004/0267228 A1* | 12/2004 | Hattori et al. ........... 604/406 |
| 2006/0052738 A1* | 3/2006 | Ramella ............... 604/19 |
| 2007/0258960 A1* | 11/2007 | DeAngelo et al. ........ 424/93.7 |

* cited by examiner

*Primary Examiner*—Krishnan S Menon
(74) *Attorney, Agent, or Firm*—Kusner & Jaffe; Michael A. Centanni (57) ABSTRACT

A multi-chamber chemical delivery container for storing dry chemicals that are used to produce a liquid microbial deactivation fluid. The container includes two housing sections and a dividing wall that is located between the two housing sections. The dividing wall separates the container into two compartments. Openings formed in each of the two housing sections are dimensioned to respectively receive an inlet fitting and an outlet fitting. The inlet and outlet fittings are dimensioned to respectively engage with inlet and outlet connectors that are fluidly connected with a fluid circulation system of a microbial deactivation system.

19 Claims, 6 Drawing Sheets

MULTI-CHAMBER CHEMICAL DELIVERY CONTAINER

FIELD OF THE INVENTION

The present invention relates generally to microbial deactivation of articles, such as medical, dental, pharmaceutical, veterinary, or mortuary instruments and devices and, more particularly, to a container and container assembly for delivering chemistry to a processing chamber in a microbial deactivation system.

BACKGROUND OF THE INVENTION

Medical, dental, pharmaceutical, veterinary, and mortuary instruments and devices (collectively referred to herein as "articles") that are exposed to blood or other bodily fluids require thorough cleaning and microbial deactivation (e.g., decontamination or sterilization) between each use. Liquid microbial deactivation systems (e.g., a reprocessor) are now widely used for microbial deactivation of articles that cannot withstand the high temperatures of a steam sterilization system. Liquid microbial deactivation systems typically operate by exposing the articles to a liquid deactivating fluid, such as peracetic acid or other strong oxidant.

Articles that are to be deactivated are placed directly within a deactivation chamber of a microbial deactivation system or inside a container that is inserted into the deactivation chamber. During a deactivation cycle, a liquid deactivating fluid is circulated through a fluid circulation system that includes the deactivation chamber and the container located therein. The liquid deactivating fluid can be introduced into the microbial deactivation system as a pre-formed solution that requires no further dilution or mixing. However, in many microbial deactivation systems, the liquid deactivating fluid is formed inside the microbial deactivation system by dissolving dry chemicals within a liquid. For example, a dry chemical reagent (e.g., acetylsalicylic acid) and a dry builder component (e.g., sodium perborate) are combined together with water to form a liquid deactivating fluid (e.g., peracetic acid) at a desired concentration.

In many systems, a chemical delivery container is used to store the dry chemical reagent and dry builder component. Prior art chemical delivery containers include numerous components and assembly steps, thus resulting in a complicated and time-consuming manufacturing process.

The present invention provides a multi-chamber chemical delivery container that overcomes the drawbacks of prior art chemical delivery containers and provides further advantages.

SUMMARY OF THE INVENTION

In accordance with a first aspect of the present invention, there is provided a container for storing chemicals for use in a microbial deactivation system, the container comprising: a first housing section including a first wall and a first opening formed in the first wall; a second housing section including a second wall with a second opening formed therein; a dividing wall disposed between said first housing section and said second housing section, wherein the dividing wall and the first wall define a first chamber for storing a first chemical and the dividing wall and the second wall define a second chamber for storing a second chemical, said dividing wall including a filter membrane; a first fitting disposed within the first opening to define an inlet; and a second fitting disposed within the second opening to define an outlet.

According to another aspect of the present invention, there is provided a container assembly for use in a microbial deactivation system, the container assembly comprising: (a) a container including a first housing section having a first wall with a first opening formed therein, a second housing section having a second wall with a second opening formed therein, a dividing wall disposed between said first housing section and said second housing section, wherein the dividing wall and the first wall define a first chamber for storing a first chemical and the dividing wall and the second wall define a second chamber for storing a second chemical, said dividing wall including a filter membrane; a first fitting disposed within the first opening to define an inlet, and a second fitting disposed within the second opening to define an outlet; (b) an inlet connector engageable with said first fitting to fluidly connect the first chamber with an inlet conduit; and (c) an outlet connector engageable with said second fitting to fluidly connect the first chamber with an outlet conduit.

An advantage of the present invention is the provision of a chemical delivery container that requires fewer components than existing chemical delivery containers.

Another advantage of the present invention is the provision of a chemical delivery container that requires fewer assembly steps than existing chemical delivery containers.

Still another advantage of the present invention is the provision of a chemical delivery container that can be manufactured quickly and simply.

A still further advantage of the present invention is the provision of a chemical delivery container that facilitates shipping and handling of the container.

Still another advantage of the present invention is the provision of a chemical delivery container that facilitates proper mixing and dissolving of dry chemicals used to produce a liquid microbial deactivating fluid.

Yet another advantage of the present invention is the provision of a chemical delivery container that has barrier properties to provide increased shelf life and maintain stability.

These and other advantages will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figures 1, 2:
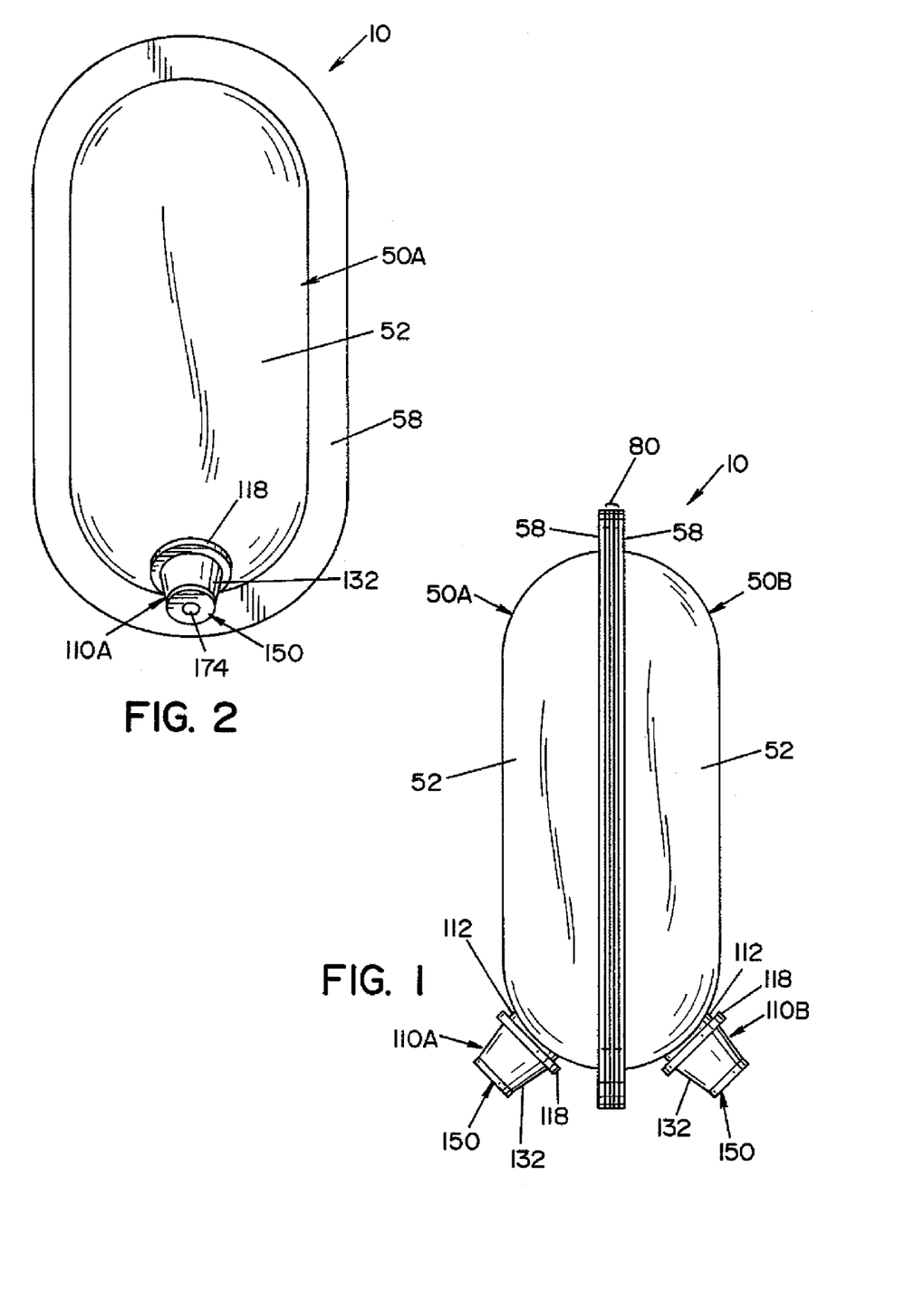
FIG. 1 is a side view of a chemical delivery container, according to an embodiment of the present invention.
FIG. 2 is a front view of the chemical delivery container.

Referring now to the drawings wherein the showings are for the purpose of illustrating the invention only, and not for the purpose of limiting same, FIG. 1 shows a chemical delivery container 10, according to one embodiment of the present invention. Chemical delivery container 10 contains dry chemicals that are used to produce a liquid microbial deactivating fluid (e.g., a liquid disinfectant or sterilant) in a liquid microbial deactivation system, such as a reprocessor. In this respect, chemical delivery container 10 is fluidly connected with a fluid circulation system of the liquid microbial deactivation system. The fluid circulation system circulates fluid (e.g., water) through chemical delivery container 10 to produce a liquid microbial deactivating fluid to effect microbial deactivation of articles (such as medical instruments and devices) located in a deactivating chamber.

Figure 3:
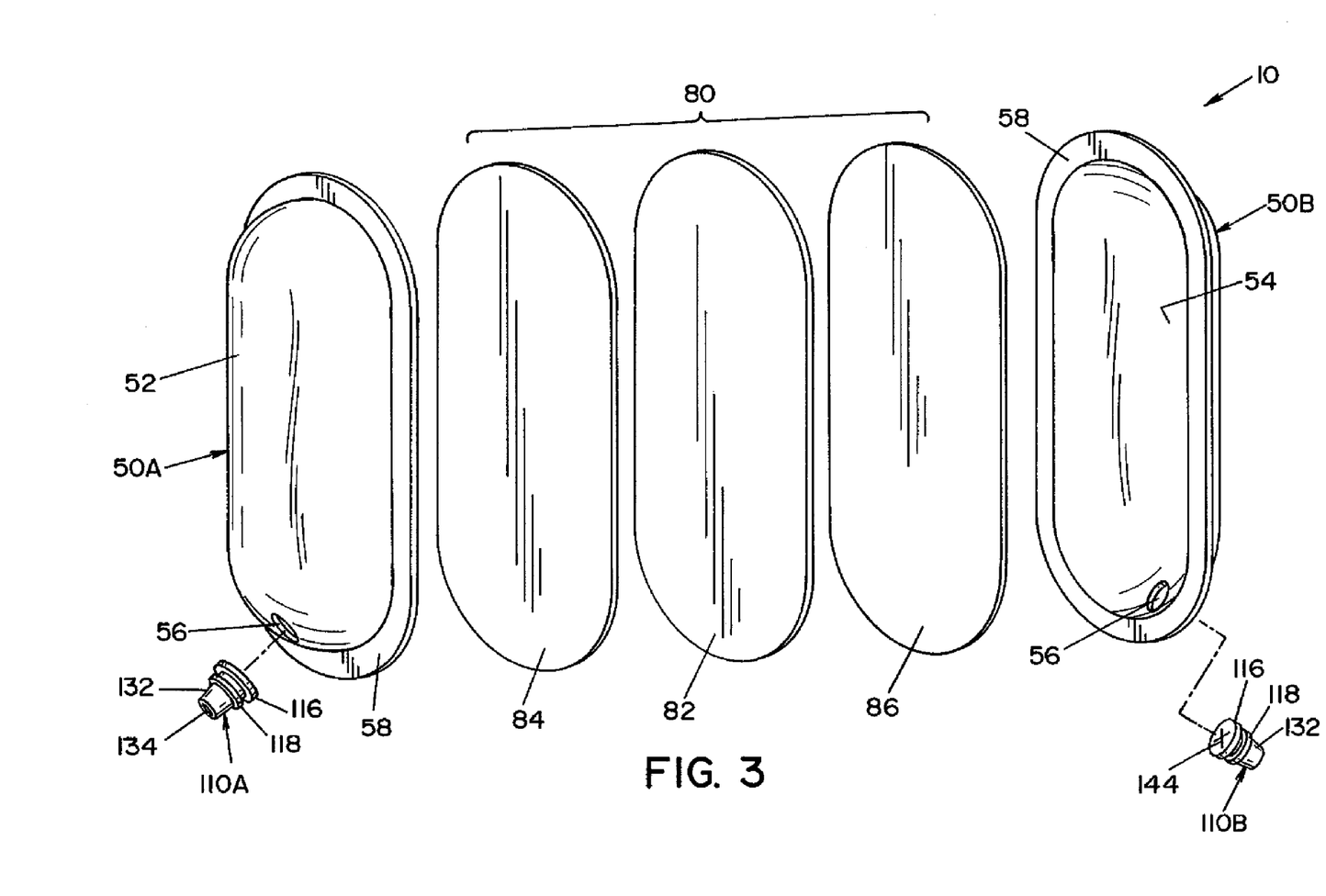
FIG. 3 is an exploded view of the chemical delivery container.

Chemical delivery container 10 is generally comprised of a first housing section 50A, a second housing section 50B, a dividing wall 80, and first and second fittings 110A, 110B, as shown in FIGS. 1-3. First housing section 50A and second housing section 50B are substantially identical, such that second housing section 50B can be understood from a description of first housing section 50A. Accordingly, only first housing section 50A is described in detail herein. Furthermore, in the drawings, components of second housing section 50B bear the same reference numbers as similar components of first housing section 50A.

First housing section 50A includes a generally cup-shaped wall 52 having a generally concave inner surface 54, as best seen in FIG. 3. A flange 58 extends outward from the periphery of wall 52. An opening 56, dimensioned to receive first fitting 110A, is formed in wall 52, as best seen in FIG. 3. First fitting 110A is described in detail below.

In one embodiment of the present invention, first housing section 50A is formed of a relatively flexible material that also provides a barrier to moisture and gas/vapor transmission (e.g., a polymeric film). A relatively flexible material is advantageous since it allows empty containers 10 to be easily compacted. First housing section 50A may also be formed of a composite film material having plurality of layers. First housing section 50A preferably includes a material that minimizes the transmission of gases and vapors (e.g., water vapor) therethrough. For instance, one layer of a composite film material may include a metallic material deposited onto a polymer or be formed of metal foil. It is also contemplated that first housing section 50A may be alternatively formed of a rigid or semi-rigid material, such as ABS (acrylonitrile butadiene styrene), polypropylene and other injection molded plastics.

Dividing wall 80 will now be described in detail with reference to FIG. 3. In the illustrated embodiment, dividing wall 80 is basically comprised of a filter membrane 82, a first support member 84 and a second support member 86. Filter membrane 82 is located between support members 84 and 86. Particles of a predetermined size are filtered by filter membrane 82. In one embodiment of the present invention, filter membrane 82 is a 0.8 polyethersulfone (PES) membrane for capturing particles greater than about 0.8 μm. PES allows high fluid flow rates at low pressure drops. By way of example and not limitation, filter membrane 82 may also be formed of polypropylene; polyethylene; nylon; rayon; a rigid porous media, such as POREX™; a porous plastic; fabric; felt; mesh; and the like. Support members 84 and 86 provide support for filter membrane 82. In one embodiment of the present invention, support members 84 and 86 take the form of a mesh-like material that allows particles and fluids to pass therethrough. For example, support members 84 and 86 may take the form of a polypropylene mesh. It is also contemplated that support members 84, 86 could be made of a material that allows fluids to flow therethrough but captures some particles, such as the materials identified above for filter membrane 82.

Figure 4:
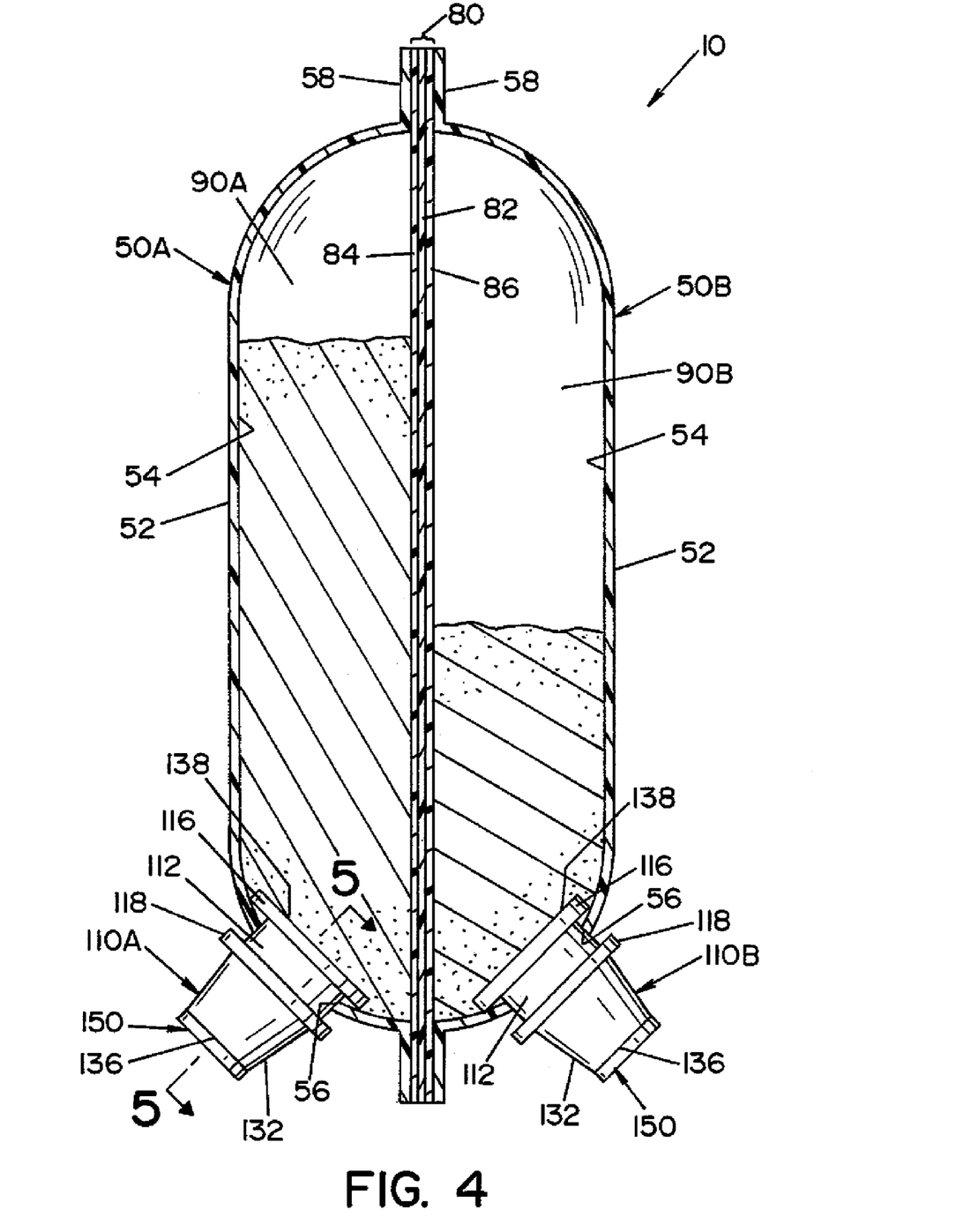
FIG. 4 is a sectional side view of the chemical delivery container, showing dry chemicals disposed therein.

First and second fittings 110A, 110B are respectively associated with first and second housing sections 50A, 50B, as shown in FIGS. 1, 3 and 4. In the illustrated embodiment, fittings 110A and 110B respectively define an inlet and an outlet of container 10. It should be understood that first fitting 110A and second fitting 110B are substantially identical, such that second fitting 110B can be understood from a description of first fitting 110A. Accordingly, only first fitting 110A is described in detail herein. Furthermore, in the drawings, components of second fitting 110B bear the same reference numbers as similar components of first fitting 110A.

By way of example and not limitation, first fitting 110A may be formed of ABS, polypropylene or other injection molded plastics. The material of first fitting 110A should be selected to be suitable for attachment with the material of housing section 50A, e.g., by heat seal, ultrasonic weld, adhesive, etc.

Figure 5:
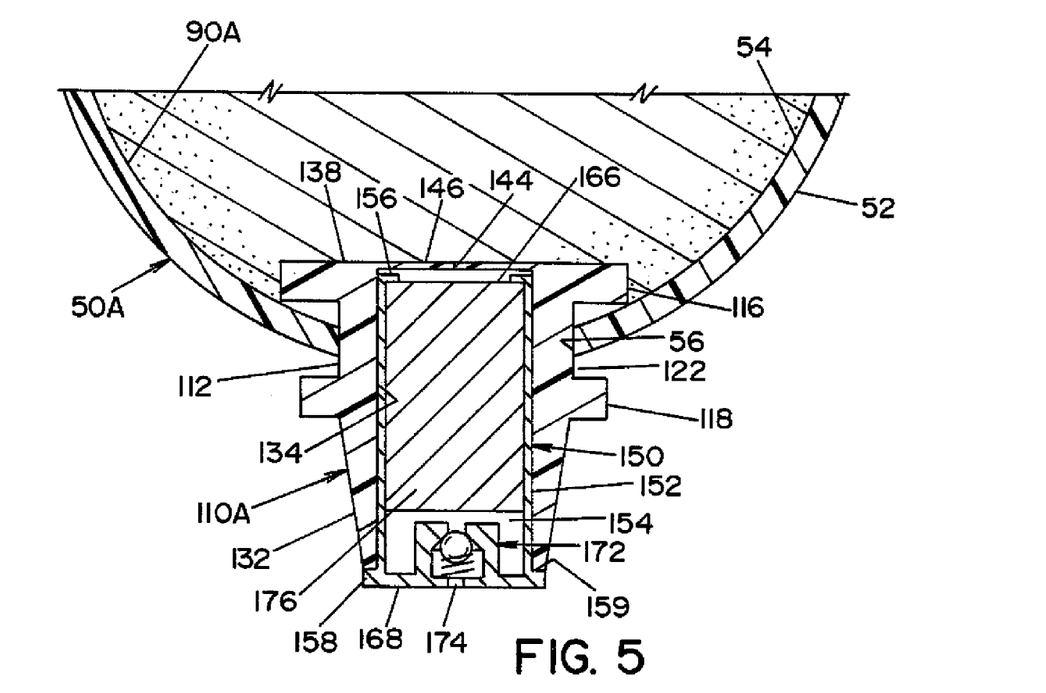
FIG. 5 is an enlarged sectional view of the chemical delivery container, taken along lines 5-5 of FIG. 4.

First fitting 110A will now be described in detail with reference to FIGS. 5 and 6. Fitting 110A is generally tube-shaped and has a first end 136 and a second end 138. A cylindrical recess 134, extending along the longitudinal axis of fitting 110A, defines an internal passageway. Fitting 110A includes a first section 112 having a generally cylindrical shape and a second section 132 having a frusto-conical outer surface. First and second annular flanges 116 and 118 extend outward from the outer surface of first section 112. Flanges 116, 118 are spaced apart to form an annular channel 122 around the outer surface of first section 112. Cylindrical recess 134 is open at first end 136 of fitting 110A and closed at second end 138 of fitting 110A. A barrier member 142 blocks recess 134 at second end 138. In the illustrated embodiment, barrier member 142 is an integral portion of first section 112 and is formed by injection molding. A plurality of slots 144 are formed in barrier member 142, thereby dividing barrier member 142 into a plurality of wall sections 146. Slots 144 are dimensioned to prevent particles from passing through barrier member 142, but allow the passage of vapor and gas therethrough. Wall sections 146 can be separated to open second end 138, as will be described in detail below. First fitting 110A is dimensioned to be received into opening 56 of first housing section 50A. As best seen in FIG. 5, fitting 110A is press fit into opening 56, such that wall 52 is captured in channel 122 between flanges 116 and 118, thereby forming a seal. Similarly, second fitting 110B is dimensioned to be received into opening 56 of housing section 50B.

It is contemplated that in an alternative embodiment of fitting 110A, barrier member 142 may be an individual component formed of a filter material (e.g., felt) that traps particles, but allows passage of vapor and gas. The filter material may be "scored" or perforated to facilitate separation thereof in order to form an opening in recess 134 at second end 138 of fitting 110A. In this alternative embodiment barrier member 142 may be formed as an additional layer of thin film, laminate, or foil that is attached to second end 138 via heat seal, ultrasonic weld, adhesive, etc.

The inlet and outlet, respectively, defined by fittings 110A and 110B are sealed by removable insert members 150 that are dimensioned to be received within cylindrical recess 134 of fittings 110A and 110B (see FIG. 5). Insert member 150 includes a cylindrical body 152 that defines an inner recess 154. Cylindrical body 152 has a first end 166 and a second end 168. Inner recess 154 is dimensioned to receive a desiccant packet 176. Desiccant packet 176 is made of conventionally known materials for absorbing moisture. An annular flange 156 extends inwardly at first end 166 of cylindrical body 152. An annular flange 158 extends outward from a second end 168 of cylindrical body 152. Outward extending annular flange 158, together with the outer surface of cylindrical body 152, define an annular shoulder 159. Annular shoulder 159 is dimensioned to abut second section 132 of fittings 110A, 110B. Insert member 150 also includes a valve member 172 disposed in inner recess 154 at second end 168 of cylindrical body 152. Valve member 172 controls fluid flow through inner recess 154 via an opening 174, thereby providing means for relieving pressure. In the illustrated embodiment, valve member 172 is a check valve. Valve member 172 is responsive to fluid pressure, such that fluid is allowed to pass from inner recess 154 to outside chemical delivery container 10. However, valve member 172 does not allow fluid flow in the opposite direction, i.e., from outside chemical delivery container 10 into inner recess 154. Inwardly extending annular flange 156 and valve member 172 capture desiccant packet 176 within inner recess 154. Insert member 150 is dimensioned to allow convenient removal from fittings 110A and 110B.

Assembly of chemical delivery container 10 will now be described with reference to FIG. 3-6. First housing section 50A and second housing section 50B are oriented, such that respective inner surfaces 54 and openings 56 face each other, as shown in FIG. 3. Dividing wall 80, comprised of filter membrane 82 sandwiched between first and second support members 84 and 86, is disposed between first housing section 50A and second housing section 50B. The peripheral edge of dividing wall 80 is aligned with flanges 58 of first and second housing sections 50A, 50B. Accordingly, the outer edge of dividing wall 80 is captured between flange 58 of first housing section 50A and flange 58 of second housing section 50B. By way of example and not limitation, flanges 58 and dividing wall 80 may be attached at their respective peripheral edges by such means as ultrasonic welding, heat sealing, an adhesive, or a combination thereof. It should be appreciated that a single integral seal can be used to attach housing sections 50A, 50B and dividing wall 80.

As best seen in FIG. 4, first housing section 50A and dividing wall 80 define a first chamber 90A of container 10. Likewise, second housing section 50B and dividing wall 80 define a second chamber 90B of container 10. Chambers 90A and 90B store dry chemicals (typically in powder form) that are dissolved together with a liquid (e.g., water) to form a liquid deactivating agent (e.g., peracetic acid). Chambers 90A and 90B are filled with the dry chemicals through respective openings 56 of first and second housing sections 50A, 50B.

In the illustrated embodiment, each chamber 90A, 90B has a volume of approximately 24 cubic inches. However, the quantity of dry chemistry may vary in each chamber. For instance, chamber 90A may contain 18 cubic inches of a first dry powdered chemical, while chamber 90B may contain only 8 cubic inches of a second dry powdered chemical having a particle size that is smaller than the particle size of the first dry powdered chemical.

It should be appreciated that the dry chemicals may include, but are not limited to, chemical reagents, builder components, buffers, inhibitors, and wetting agents. In the illustrated embodiment of the present invention, chamber 90A is filled with a chemical reagent (e.g., acetylsalicylic acid), while chamber 90B is filled with builder components (e.g., sodium perborate). When the chemical reagent and the builder components are combined together with a liquid (e.g., water), a liquid microbial deactivating fluid (e.g., peracetic acid) is formed.

After first and second chambers 90A and 90B have been filled with an appropriate quantity of dry chemicals, fittings 110A, 110B are inserted into respective openings 56 of first and second housing sections 50A, 50B. An insert member 150 is inserted into recess 134 of each fitting 110A, 110B, before or after fittings 110A, 110B are inserted into their respective openings 56. As discussed above, insert member 150 has a desiccant packet 176 therein.

Figure 6:
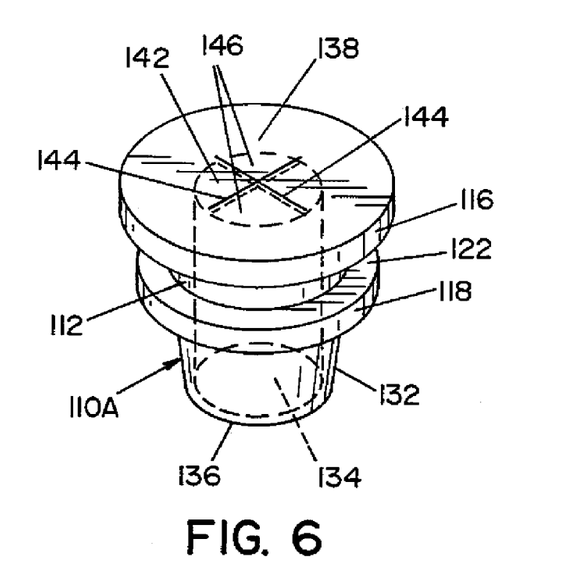
FIG. 6 is a perspective view of a fitting.

Fitting 110A is press fit into opening 56 of first housing section 50A and is retained therein by capturing wall 52 of first housing section 50A in annular channel 122, between flanges 116, 118, as shown in FIGS. 5 and 6. In a similar manner, fitting 110B is press fit into opening 56 of second housing section 50B. Flanges 116, 118 and cylindrical section 112 are dimensioned to form a seal around the periphery of opening 56. It is also contemplated that additional sealant material (e.g., an adhesive) may be inserted in the region between fittings 110A and 110B and the periphery of openings 56.

Barrier members 142 of fittings 110A, 110B prevent the release of dry chemical particles from chambers 90A and 90B. However, slots 144 formed in barrier members 142 allow excess vapor and gas within chambers 90A and 90B to pass therethrough. In response to increased pressure inside recess 154, check valve 172 opens, thereby releasing the excess vapor and gas. In this manner, gases that expand or are generated within chambers 90A, 90B are released from chamber 10 before excessive pressure can cause damage to container 10.

An inlet connector 210 and an outlet connector 260 are connected with container 10 to form a container assembly. Inlet connector 210 and outlet connector 260 will now be described with reference to FIGS. 7 and 8. Inlet connector 210 and outlet connector 260 are dimensioned to respectively connect to one of fittings 110A or 110B. In the illustrated embodiment, inlet connector 210 is connected to fitting 110A, while outlet connector 260 is connected to fitting 110B. However, it is contemplated that the connections may be reversed. It is also contemplated that inlet connector 210, outlet connector 260, first fitting 110A, and second fitting 110B may be dimensioned such that each connector 210, 260 will mate properly with only one of the fittings 110A, 100B.

Figure 7:
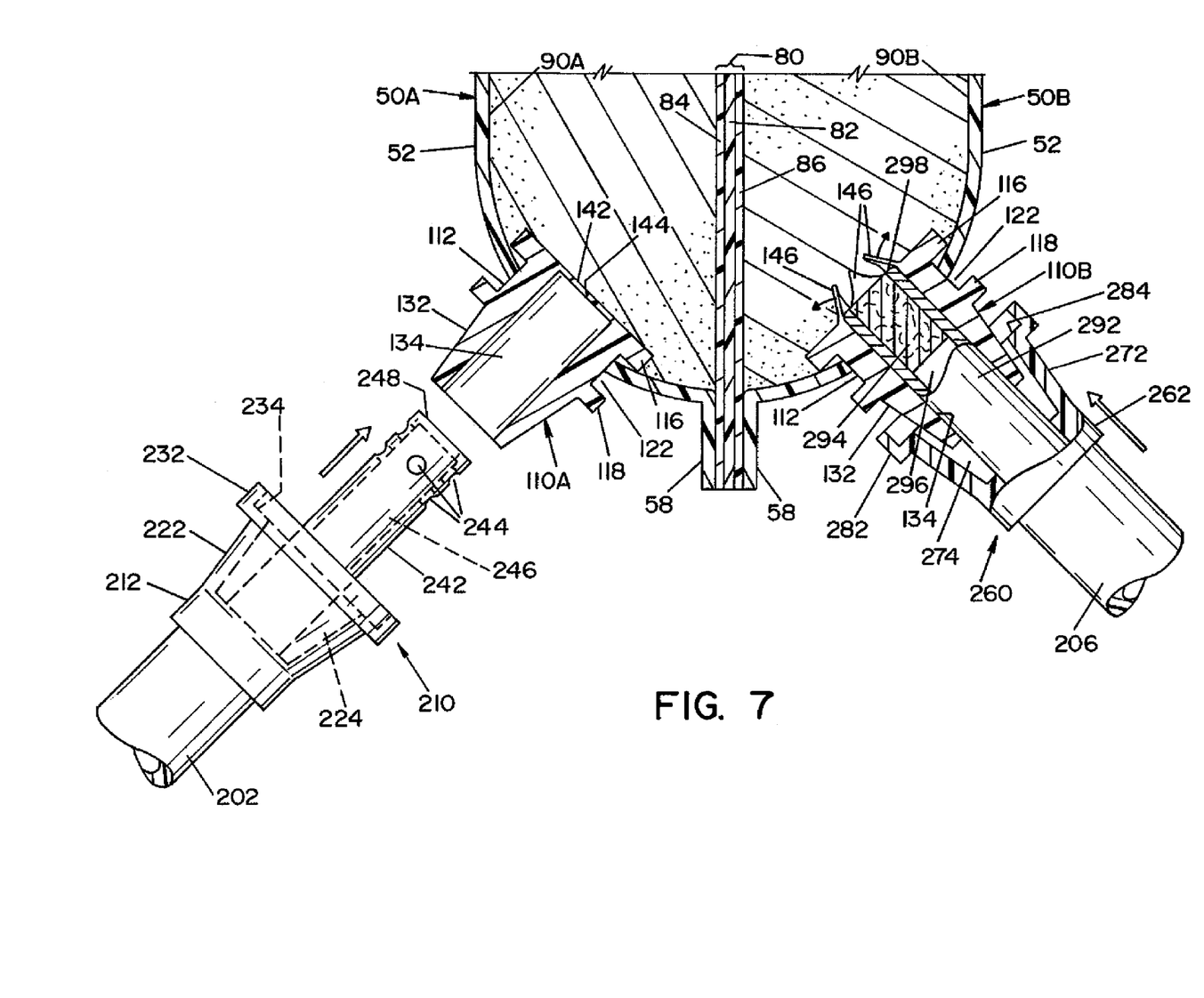
FIG. 7 illustrates a container assembly including an enlarged, sectional view of a portion of the chemical delivery container, showing mating inlet and outlet connectors.
Figure 8:
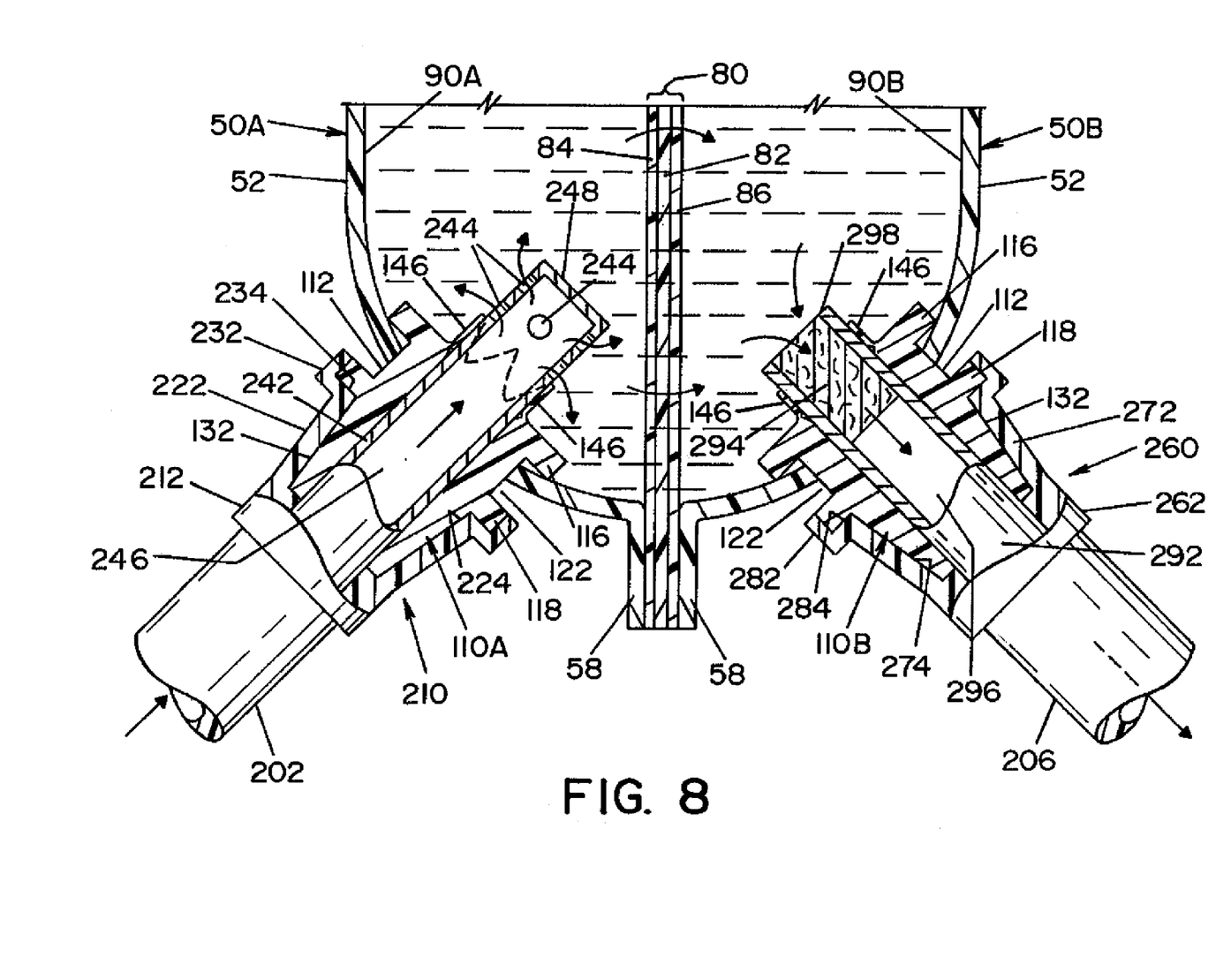
FIG. 8 illustrates the container assembly of FIG. 7, including a sectional view of a portion of the chemical delivery container, showing engagement with mating inlet and outlet connectors and fluid flow through the chemical delivery container.

When inlet connector 210 is connected to fitting 110A, an inlet hose or tube 202 is put in fluid communication with first chamber 90A of container 10. Likewise, when outlet connector 260 is connected to fitting 110B, an outlet hose or tube 206 is put in fluid communication with chamber 90B of container 10. Inlet tube 202 and outlet tube 206 are connected with a fluid circulation system (not shown) of a liquid microbial deactivation system.

Inlet connector 210 is generally comprised of an annular base portion 212, a collar section 222 having a generally frusto-conical shape, and a cylindrical stem 242. Inlet tube 202 is fixed to base portion 212 by conventionally known means. Collar section 222 defines a conical recess 224. An annular flange portion 232, formed at one end of collar section 222, defines an annular seat 234. Cylindrical stem 242 extends outward from base portion 212, through conical recess 224, beyond flange portion 232, as best seen in FIG. 7. An inner conduit 246 is defined by cylindrical stem 242. One end of cylindrical stem 242 is open to provide fluid communication with inlet tube 202. The opposite end 248 of cylindrical stem 242 is closed. A plurality of openings 244 are formed in cylindrical stem 242, as shown in FIG. 7. Openings 244 act as "nozzles" or "jets" to spray liquid therethrough, as will be described in further detail below. In the illustrated embodiment, a plurality of openings 244 are arranged radially around cylindrical stem 242 to spray liquid in multiple directions.

As shown in FIG. 8, cylindrical stem 242 of inlet connector 210 is dimensioned to be received within cylindrical recess of fitting 110A. Furthermore, collar section 222 of inlet connector 210 is dimensioned to receive second section 132 of fitting 110A, and annular seat 234 of inlet connector 210 is dimensioned to receive second flange 118 of fitting 110A. As inlet connector 210 is fully inserted into fitting 110A, cylindrical stem 242 penetrates barrier member 142, thereby separating wall sections 146. When inlet connector 210 is in a fully inserted position, end 248 of cylindrical stem 242 is received within first chamber 90A of container 10, second section 132 of fitting 110A is received within recess 224 of inlet connector 210, and second flange 118 of fitting 110A is received within annular seat 234 of inlet connector 210. Openings 244 of cylindrical stem 242 are located within first chamber 90A to spray liquid therein.

Outlet connector 260 is generally comprised of an annular base portion 262, a collar section 272 having a generally frusto-conical shape, and a cylindrical stem 292. Outlet tube 206 is fixed to base portion 262 by conventionally known means. Collar section 272 defines a conical recess 274, as best seen in FIG. 7. An annular flange portion 282, formed at one end of collar section 272, defines an annular seat 284. Cylindrical stem 292 extends outward from base portion 262, through conical recess 274, beyond flange portion 282, as best seen in FIG. 7. An inner conduit 296 is defined by cylindrical stem 292. One end of cylindrical stem 292 is open to provide fluid communication with outlet tube 206. The opposite end 298 of cylindrical stem 292 has an opening dimensioned to receive a filter member 294. Filter member 294 is dimensioned to allow liquids to pass through while blocking solid particulate matter. By way of example and not limitation, filter member 294 is formed of felt or other filter material, such as porous plastic.

As shown in FIG. 8, cylindrical stem 292 of outlet connector 260 is dimensioned to be received within cylindrical recess of fitting 110B. Furthermore, collar section 272 of outlet connector 260 is dimensioned to receive second section 132 of fitting 110B, and annular seat 284 of outlet connector 260 is dimensioned to receive second flange 118 of fitting 110B. As outlet connector 260 is fully inserted into fitting 110B, cylindrical stem 292 penetrates barrier member 142, thereby separating wall sections 146. When outlet connector 260 is in a fully inserted position, end 298 of cylindrical stem 292 is received within first chamber 90B of container 10, second section 132 of fitting 110B is received within recess 274 of outlet connector 260, and second flange 118 of fitting 110B is received within annular seat 284 of outlet connector 260.

Operation of chemical delivery container 11 in connection with a liquid microbial deactivation system, such as a reprocessor, will now be described. Before connecting container 10 with inlet connector 210 and outlet connector 260 of a liquid microbial deactivation system, insert member 150 (including desiccant packet 176) is removed from recess 134 of each fitting 110A and 110B. Inlet connector 210 is then connected with fitting 110A by inserting cylindrical stem 242 into recess 134 of fitting 110A. As indicated above, when inlet connector 210 is fully inserted into fitting 110A, end 248 of cylindrical stem 242 is received within first chamber 90A of container 10, second section 132 of fitting 110A is received within recess 224 of inlet connector 210, and second flange 118 of fitting 110A is received within annular seat 234 of inlet connector 210. Likewise, outlet connector 260 is connected with fitting 110B by inserting cylindrical stem 292 into recess 134 of fitting 110B. As indicated above, when outlet connector 260 is fully inserted into fitting 110B, end 298 of cylindrical stem 292 is received within first chamber 90B of container 10, second section 132 of fitting 110B is received within recess 274 of outlet connector 260, and second flange 118 of fitting 110B is received within annular seat 284 of outlet connector 260.

After completing the connection of inlet connector 210 to fitting 110A and the connection of outlet connector 260 to fitting 110B, container 10 may be disposed within a deactivation compartment of the liquid microbial deactivation system. It is also contemplated that container 10 can be dimensioned to automatically engage with inlet connector 210 and outlet connector 260 upon placement of container 10 into the deactivation compartment, thereby eliminating the need for manually connecting inlet connector 210 to fitting 110A and outlet connector 260 to fitting 110B.

Liquid microbial deactivation system may be operated such that the fluid circulation system pumps water (or other liquid) through inlet tube 202 to inlet connector 210. The water is forced through openings 244 of cylindrical stem 242 to spray water into first chamber 90A. Openings 244 promote circulation and turbulent flow of water inside first chamber 90A, thereby facilitating mixing of the water with the dry chemicals. The dry chemicals inside first chamber 90A dissolve in the water to form a first chemical solution that passes through dividing wall 80 into second chamber 90B. Filter membrane 82 captures undissolved particles in the first chemical solution and prevents their passage into second chamber 90B. The capture of undissolved particles helps extend the life of other filters of the liquid microbial deactivation system, by removing particles that may clog filters of the deactivation system. Inside second chamber 90B, the first chemical solution mixes with the dry chemicals stored in second chamber 90B to form a second chemical solution that takes the form of a liquid deactivating fluid. The liquid deactivating fluid inside second chamber 90B flows into outlet tube 206 through outlet connector 260. Filter member 294 removes solid particulate matter from the liquid deactivating fluid before the liquid deactivating fluid reaches outlet tube 206. Accordingly, filter member 294 prevents undissolved dry chemicals from entering the fluid circulation system. The liquid deactivating fluid inside outlet tube 206 is circulated through the fluid circulation system to effect a microbial deactivation.

The foregoing is one embodiment of the present invention. It should be appreciated that this embodiment is described for purposes of illustration only and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. A container for a first and second dry powdered chemical for use in a microbial deactivation system, said first dry powdered chemical forming a first chemical solution when mixed with a fluid and said second dry powdered chemical forming a liquid microbial deactivation fluid when mixed with said first chemical solution, the container comprising:

a first housing section including a first wall and a first opening formed in the first wall;

a second housing section including a second wall with a second opening formed therein;

a dividing wall having first and second opposing surfaces, said dividing wall captured by said first housing section and said second housing section, wherein said first surface is in contact with said first housing section and said second surface is in contact with said second housing section and wherein the dividing wall and the first wall define a first chamber for storing said first dry powdered chemical, and the dividing wall and the second wall define a second chamber for storing said second dry powdered chemical, said dividing wall including a filter membrane for allowing said first chemical solution to pass therethrough and for preventing said first and second dry powdered chemicals from passing therethrough;

a first fitting adapted to receive a connector, said first fitting disposed within said first opening and having a barrier element formed therein, wherein said barrier element prevents said first, dry powdered chemical from passing therethrough but allows vapor and gas to pass therethrough; and a second fitting adapted to receive a connector, said second fitting disposed within said second opening and having a barrier element formed therein, wherein said barrier element prevents said second, dry powdered chemical from passing therethrough but allows vapor and gas to pass therethrough.

2. A container as defined in claim 1, wherein said dividing wall further comprises first and second support members in contact with opposing sides of said filter membrane, said first support member defining said first surface of said dividing wall and said second support member defining said second surface of said dividing wall.

3. A container as defined in claim 1, wherein said first and second housing sections respectively include first and second flanges extending along the periphery of the first and second walls, wherein said first surface of said dividing wall is in contact with said first flange and said second surface of said dividing wall is in contact with said second flange.

4. A container as defined in claim 1, wherein each of said first and second fittings includes:
an internal passageway;
a first end open to the internal passageway; and
a second end having said barrier element disposed therein, wherein said barrier element is penetrable to open the second end of said first and second fittings.

5. A container as defined in claim 4, wherein each of said first and second fittings includes:
first and second spaced-apart annular flanges, said spaced-apart annular flanges dimensioned to capture a portion of one of said first and second walls.

6. A container according to claim 4, wherein said container further comprises:
a removable insert member disposed within each of said internal passageways of said first and second fittings, wherein said insert member captures moisture.

7. A container according to claim 6, wherein said insert member includes:
an inner recess dimensioned to receive a desiccant; and
a valve member.

8. A container according to claim 7, wherein said valve member is a check valve.

9. A container as defined in claim 1, wherein said first housing section and said second housing section are formed of a polymeric film.

10. A container as defined in claim 9, wherein said polymeric film is a composite film having a plurality of layers.

11. A container as defined in claim 9, wherein said first and second housing sections are comprised of an injection molded plastic.

12. A container as defined in claim 1, wherein said filter membrane is comprised of polyethersulfone (PES).

13. A container assembly for a first and second dry powdered chemical for use in a microbial deactivation system, said first dry powdered chemical forming a first chemical solution when mixed with a fluid and said second dry powdered chemical forming a liquid microbial deactivation fluid when mixed with said first chemical solution, the container assembly comprising:
a container including:
a first housing section having a first wall with a first opening formed therein,
a second housing section having a second wall with a second opening formed therein,
a dividing wall disposed between said first housing section and said second housing section, wherein the dividing wall and the first wall define a first chamber for storing said first dry powdered chemical, and the dividing wall and the second wall define a second chamber for storing said second dry powdered chemical, said dividing wall including a filter membrane;
a first fitting disposed within the first opening to define an inlet, and
a second fitting disposed within the second opening to define an outlet;
an inlet connector engageable with said first fitting to fluidly connect the first chamber with an inlet conduit, said inlet connector including a stem portion defining a recess, said stem portion having a plurality of openings arranged radially around the stem portion to allow fluid to flow out of said recess in multiple directions, said stem portion extending through said first fitting and being disposed within said first chamber when said inlet connector engages said first fitting; and
an outlet connector engageable with said second fitting to fluidly connect the second chamber with an outlet conduit.

14. A container assembly as defined in claim 13, wherein said outlet connector includes:
a stem portion defining a recess, said stem portion having an opening therein for receiving fluid into the recess.

15. A container assembly as defined in claim 14, wherein said outlet connector includes a filter member inside said recess, said filter member allowing said liquid microbial deactivation fluid to flow therethrough but preventing said first and second dry powdered chemicals from passing therethrough.

16. A container assembly as defined in claim 13, wherein each of said first and second fittings includes:
an internal passageway;
a first end open to the internal passageway; and
a second end having a barrier for blocking the internal passageway, wherein said barrier is penetrable to open the second end.

17. A container assembly for a first and second dry powdered chemical for use in a microbial deactivation system, said first dry powdered chemical forming a first chemical solution when mixed with a fluid and said second dry powdered chemical forming a liquid microbial deactivation fluid when mixed with said first chemical solution, the container assembly comprising:
a container comprised of:
a first housing section having a first wall with a first opening formed therein, a second housing section having a second wall with a second opening formed therein, a dividing wall disposed between said first housing section and said second housing section, wherein the dividing wall and the first wall define a first chamber for storing said first dry powdered chemical, and the dividing wall and the second wall define a second chamber for storing said second dry powdered chemical, said dividing wall including a filter membrane, a first fitting disposed within the first opening to define an inlet, and a second fitting disposed within the second opening to define an outlet;

an inlet connector engageable with said first fitting to fluidly connect the first chamber with an inlet conduit; and an outlet connector engageable with said second fitting to fluidly connect the second chamber with an outlet conduit, said outlet connector including a stem portion defining a recess and a filter membrane inside said recess, said stem portion extending through said second fitting and being disposed within an inner portion of said second chamber when said outlet connector engages said second fitting, said filter membrane allowing said liquid microbial deactivation fluid to pass therethrough but preventing said first and second dry powdered chemicals from passing therethrough.

18. A container assembly as defined in claim 17, wherein said inlet connector includes:

a stem portion defining a recess, said stem portion having a plurality of openings formed therein to allow fluid flow out of said recess, said stem portion extending through said first fitting and being disposed within said first chamber when said inlet connector engages said first fitting.

19. A container assembly as defined in claim 17, wherein each of said first and second fittings include:

an internal passageway;

a first end open to the internal passageway; and a second end having a barrier for blocking the internal passageway, wherein said barrier is penetrable to open the second end.

\* \* \* \* \*